United States Patent [19]

Mazzagatti

[11] 4,367,440
[45] Jan. 4, 1983

[54] HIGH PERCENTAGE WATER CONTENT MONITOR

[75] Inventor: Roy P. Mazzagatti, Bellaire, Tex.

[73] Assignee: Texaco Inc., White Plains, N.Y.

[21] Appl. No.: 197,880

[22] Filed: Oct. 17, 1980

[51] Int. Cl.³ .......................................... G01N 27/42
[52] U.S. Cl. ................................................. 324/445
[58] Field of Search ............... 324/445, 449, 450, 442, 324/439, 425

[56] References Cited

U.S. PATENT DOCUMENTS 3,404,336 10/1968 Rosenthal ........................... 324/445
4,220,920 9/1980 Gross ................................... 324/445

Primary Examiner—Michael J. Tokar

Attorney, Agent, or Firm—Carl G. Ries; Robert A. Kulason; Ronald G. Gillespie

[57] ABSTRACT

A monitor which is capable of measuring accurately the water content in percent by volume of an oil and brine mixture, where the water content is 80% or more, includes a housing which is adapted to be connected to a pipe through which the oil and brine mixture is flowing so that the oil and brine mixture flows through a portion of the housing. A sensor is mounted within the housing so that the sensor is suspended in the flowing oil and brine mixture. The sensor provides a signal corresponding to the percent by volume of water in the oil and brine mixture, even when percent by volume of water is 80% or more, in response to an excitation voltage from a source. Indicating apparatus provides an indication of the percent by volume of the water in the oil and brine mixture in accordance with the signal from the sensor.

7 Claims, 1 Drawing Figure

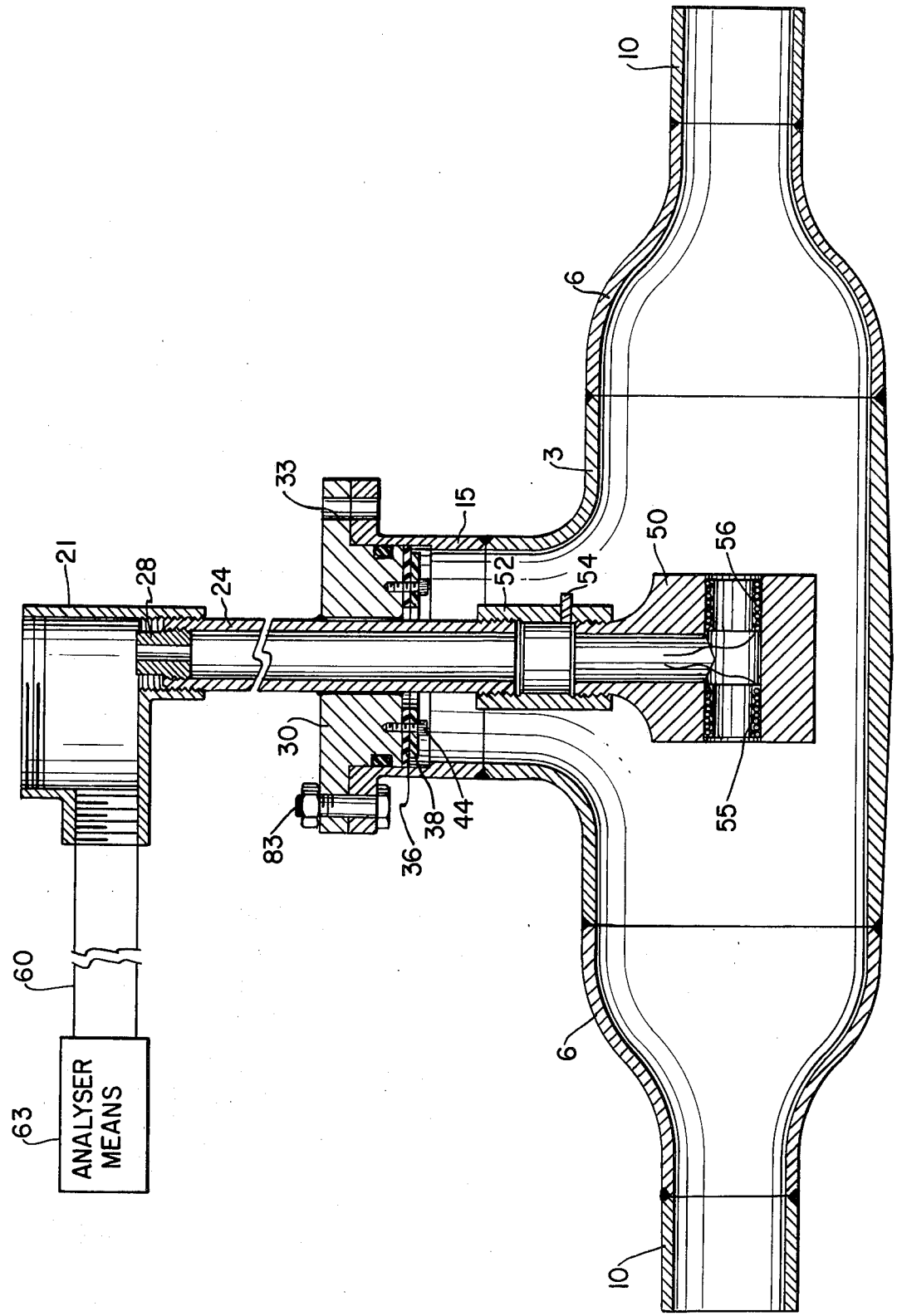

HIGH PERCENTAGE WATER CONTENT MONITOR

BACKGROUND OF THE INVENTION

Field of the Invention

The present invention relates to monitors in general and, more particularly, to crude-in-brine monitors.

SUMMARY OF THE INVENTION

An oil-in-brine monitor capable of measuring percent by volume of water in an oil-in-brine mixture in which the water content is 80% or more includes a housing which houses a sensor. The sensor receives an excitation voltage from a source and provides a signal in accordance with the water content of the oil-in-brine mixture. Apparatus provides an indication of the percent water in the mixture in accordance with the signal from the sensor.

The objects and advantages of the invention will appear more fully hereinafter, from a consideration of the detailed description which follows, taken together with the accompanying drawing wherein one embodiment is illustrated by way of example. It is to be expressly understood, however, that the drawing is for illustration purposes only and is not to be construed as defining the limits of the invention.

DESCRIPTION OF THE DRAWING

The drawing is a mechanical drawing of an oil-in-brine monitor constructed in accordance with the present invention.

DESCRIPTION OF THE INVENTION

The determination of water content in oil-in-brine mixtures is of utmost importance to the petroleum industry. In the conventional use of commercial capacitance type sensors, the devices are usually limited to applications where brine-in-oil emulsions are monitored. This effectively limits the application to a water cut of 0 to 70 percent by volume of water in oil.

For oil production water flood projects, water cut values of 80% to 100% are common. In this water cut range, where free brine is present, the capacitance type probes are not applicable. The present invention utilizes a resistivity measuring technique for determining the water content in an oil-in-brine mixture where there is a water cut range of 80% to 100%.

It should be noted where the water content of the mixture is in the vicinity of 74% to 76%, the water becomes the continuous phase which contains the oil. This type of mixture is unstable and will separate into water and oil in a relatively short time period. A water-in-oil mixture, i.e. where oil is the continuous phase, is highly stable and does not separate readily.

Referring now to the FIGURE, there is shown a monitor which for resistivity determination of water cuts in the 80% to 100% range includes a tee 3 having concentric reducers 6 welded to opposite ends. Concentric reducers 6 reduce the measuring cell size down to the pipe diameter. Victaulic adaptors 10 are welded to the narrow ends of reducers 6. A flange extension 15 is welded to the remaining open end of tee 3.

A probe assembly includes an outlet box 21 having an internal threaded end for being connected to a sensor extension arm 24. Sensor extension arm 24 also has internal threads at the end that is connected to outlet box 21 and external threads at the opposite end. A plug 28 is threaded into sensor extension arm 24 and has a passageway for the passage of wires. A probe flange 30 is welded to sensor extension arm 24 and has holes for mounting bolts 83 which are used to affix robe flange 30 to flange extension 15. A wiper 36 of neoprene rubber is held in place by a plastic retainer 38 which is affixed to probe flange 30 by screws 44. A thermistor 54 is mounted in a connector 52 which is connected to extension arm 24.

Sensor head 50 containing two toroidal coils 55 and 56, one for transmitting (coil 55) electromagnetic energy into the flowing oil-in-brine mixture and one for receiving (coil 56) the electromagnetic energy from the mixture. Head 50 may be of the type manufactured by Great Lakes Instruments, Inc. as their part number 32014 electrodeless sensor. The wires (not shown) from thermistor 54 and coils 55, 56 pass through extension arm 24 to outlet box 21 and are connected to analyzer means 63 by way of a cable in a conduit 60. Analyzer means 63, which may be of the type also manufactured by Great Lakes Instruments, Inc. as their model 75 conductivity analyzer, also provides an excitation voltage to coil 55. Analyzer means 63 provides an indication of the water content of the mixture in accordance with the signals from coil 56 and from thermistor 54.

The present invention as hereinbefore described is an oil-in-brine monitor which measures the water cut of a mixture wherein the water cut lies within the range of 80 to 100 percent.

What is claimed is:

1. An oil-in-brine mixture comprising
   housing means connected to a pipe having an oil and brine mixture flowing through the pipe in a manner so that the oil and brine mixture flows through a portion of the housing means;
   sensor means mounted within said housing means in a manner so that the sensor means will be suspended in the flowing mixture, said sensor means includes water sensing means for detecting the water content of oil and brine mixtures having a water content of 80% or more by volume and providing a sensed water signal representative thereof, and temperature sensing means for sensing the temperature of the oil and brine mixture and provides a representative temperature signal;
   means electrically connected to said sensor means for providing an excitation voltage to said sensor means; and
   means for providing an indication of the percent by volume of the water in the oil and brine mixture in accordance with the sensed water signal and the temperature signal from the sensor means.

2. A monitor as described in claim 1 in which the housing means includes
   a pair of adaptor means having approximately the same diameter as that of the pipe,
   chamber means affixed between the adaptor means and increasing in diameter from the adapting means diameter to a larger diameter of sufficient dimension to house the sensor means and having an opening with sufficient clearance for said sensor means to pass through it, and
   sealing means for sealing said sensor means within said housing means while permitting the passage of electrical conductors from the sensor means to the excitation means and to the indicating means.

3. A monitor as described in claim 2 in which the temperature sensing means is a thermistor.

4. A monitor as described in claim 3 in which the sensing means includes
   a head having a channel through which the oil flows,
   a pair of toroidal coils mounted in the channel of the mounting head, one coil receiving the excitation voltage, the other coil providing the sensed water signal in accordance with an electromagnetic field developed in the oil and brine mixture by the one coil in response to the excitation voltage,
   sensor arm means which passes through the sealing means of the housing means having threaded ends and a channel for the passage of wires,
   connector means for connecting said head means to said sensor arm means so that when said sensor head means is positioned the oil-in-brine mixture flows through it,
   the thermistor, and
   wire means for connecting the one coil to the excitation means and the other coil to the indicating means.

5. A monitor as described in claim 4 in which the sealing means includes
   flange means in which the sensor arm means is affixed and permanently sealed,
   O-ring sealing means arranged with said flange means so that when said flange means is mated with said chamber means, the O-ring means provides sealing, and
   means for fastening the flange means to said chamber means in a manner so that the head means when connected to the sensor arm by the connector passes through the opening of said chamber means and is positioned in said chamber means.

6. A method of monitoring oil-in-brine comprising the steps of
   arranging a housing with a pipe having an oil and brine mixture flowing through the pipe in a manner so that the oil and brine mixture flows through a portion of the housing,
   detecting the water content of oil and brine mixtures having a water content of 80% or more by volume with a water sensing device mounted within said housing means in a manner so that the sensing device will be suspended in the flowing mixture,
   providing a sensed water signal representative of the detected water content,
   sensing the temperature of the oil and brine mixture with a temperature sensor mounted within said housing means in a manner so that the temperature sensor will be suspended in the flowing mixture,
   providing a representative temperature signal in accordance with the sensed temperature,
   providing an excitation voltage to said water sensing device, and
   providing an indication of the percent by volume of the water in the oil and brine mixture in accordance with the sensed water signal and the sensed temperature signal.

7. A method as described in claim 6 in which the detecting step includes transmitting electromagnetic energy into the flowing oil and brine mixture in response to the excitation voltage,
   receiving the electromagnetic energy at another location in the flowing mixture within said housing, and
   providing the sensed water signal in accordance with the received electromagnetic energy.

* * * * *

UNITED STATES PATENT AND TRADEMARK OFFICE
CERTIFICATE OF CORRECTION

PATENT NO. : 4,367,440
DATED : January 4, 1983
INVENTOR(S) : ROY P. MAZZAGATTI

It is certified that error appears in the above—identified patent and that said Letters Patent is hereby corrected as shown below:

Column 2, line 32, "mixture" should read --monitor--

Signed and Sealed this

Twenty-first Day of June 1983

[SEAL]

Attest:

DONALD J. QUIGG

Attesting Officer    Acting Commissioner of Patents and Trademarks